United States Patent
Wiegand

(10) Patent No.: US 8,678,961 B2
(45) Date of Patent: Mar. 25, 2014

(54) BLOOD-TRAIL ENHANCER FOR BOW HUNTING

(76) Inventor: Gayle Wiegand, Phoenix, NY (US)

( * ) Notice: Subject to any disclaimer, the term of this patent is extended or adjusted under 35 U.S.C. 154(b) by 80 days.

(21) Appl. No.: 13/526,577

(22) Filed: Jun. 19, 2012

(65) Prior Publication Data

US 2013/0337950 A1    Dec. 19, 2013

(51) Int. Cl.
*F42B 6/08*    (2006.01)
*A01M 31/00*    (2006.01)

(52) U.S. Cl.
USPC .................................... 473/583; 43/1

(58) Field of Classification Search
USPC ................. 43/1; 124/23.1; 473/578, 583, 584
See application file for complete search history.

(56) References Cited

U.S. PATENT DOCUMENTS

| | | | |
|---|---|---|---|
| 2,467,838 A * | 4/1949 | Lust et al. | 473/581 |
| 3,066,940 A * | 12/1962 | De Lonais | 473/581 |
| 3,396,660 A | 8/1968 | Bilson et al. | |
| 3,893,866 A | 7/1975 | Hollingsworth | |
| 4,380,340 A | 4/1983 | Simo | |
| 4,597,580 A | 7/1986 | Gassie | |
| 5,202,533 A | 4/1993 | Vandersteen | |
| RE34,397 E * | 10/1993 | DelMonte et al. | 473/584 |
| 6,186,913 B1 | 2/2001 | Thomas | |
| 7,255,659 B2 | 8/2007 | Jones | |
| 2005/0233061 A1 * | 10/2005 | Schwarz | 427/2.1 |

OTHER PUBLICATIONS

Hattersley, Paul G., Activated Coagulation Time of Whole Blood, Journal of the American Medical Association, May 2, 1966, vol. 196, No. 5, pp. 150, ff.

* cited by examiner

*Primary Examiner* — John Ricci
(74) *Attorney, Agent, or Firm* — Bernhard P. Molldrem, Jr.

(57) ABSTRACT

Blood trail enhancer is composed of fish oil and apple cider vinegar together with effective amounts of natural anti-coagulant agents, such as ginger, onion, and garlic. These agents also are effective in promoting healing of a non-fatal wound in a game animal.

12 Claims, No Drawings

BLOOD-TRAIL ENHANCER FOR BOW HUNTING

FIELD OF THE INVENTION

The present invention relates generally to archery and to bowhunting, and is more particularly directed to a composition, and to a technique for applying the composition to the arrow head and a portion of the arrow shaft to inhibit coagulation of blood from the wound caused by the arrow, so that the blood trail left when the game animal is wounded but bounds off, will continue and increase the probability that the hunter will locate the animal and harvest it. The invention is also concerned with all-natural compositions applied onto the arrow so that if the arrow wound is not fatal, and the animal escapes, the probability increases that the animal's wound will heal and not become infected.

BACKGROUND OF THE INVENTION

Bowhunting is widely enjoyed, especially for hunting game animals such as white-tail deer. When hunting, the proficient bowhunter will try to direct the flight of the arrow to strike the deer (or other game animal) in a vital area, so that the arrow creates a mortal wound, and the deer dies quickly. However, the deer often escapes, even after a fatal wound, and can run for a considerable distance to seek cover somewhere in the underbrush. In that case, the hunter attempts to follow the blood trail left behind as the wounded animal moves, so the hunter can find the deer and harvest it properly.

In bowhunting, the results of a shot of an arrow at an animal can be classified in four basic types. (1) In a clean miss, where the arrow misses the animal, the deer bounds away unwounded, and the hunt for that particular animal is at an end. (2) For a clean kill shot, i.e., where the arrow is well placed in a vital organ, the wound results in an adequate blood trail which leads the hunter easily to the animal, which expires quickly from the wound. (3) A typical kill shot is a less than perfectly placed shot, but the wound results in a blood trail that will eventually dry up before leading to the animal, which will eventually expire from the wound. Every year there are thousands of deer that are killed this way, and where the hunter has to abandon the search after having spent hours trying in vain to find the animal, because the blood trail has ended before the deer can be located. (4) A non-vital shot is one that misses any vital organs, but nonetheless wounds the animal, i.e., in the rump or shoulder, for example, and where the wound, while not fatal in itself, can become infected and/or fail to heal properly. This can cause undue stress or eventually death to the animal, but will not result in harvesting of the animal by any hunter. All or nearly all bowhunters have experienced, or eventually will experience, a shot on a game animal that they know is not fatal, leaving the hunter hoping that the wounded animal survives and recovers, although often the wounded animal does succumb to the infection.

Some previous attempts to increase the blood flow from the wound on a game animal have involved modifying the arrows to increase the wound size or hold the wound open. However, these techniques involve having to use special, modified arrows or arrowheads, and cannot guarantee any success if the arrow penetrates too far or not far enough. A previous attempt to provide a blood-clot-inhibiting formulation that was to be applied to the blades of the arrow head when hunting is described in Jones U.S. Pat. No. 7,255,659. The Jones formulation was an aqueous mixture of gums and glycerine, in which the active ingredient was trisodium citrate, with small inclusions of tumeric, white willow bark, ginger and fenugreek. While the formulation was intended to inhibit blood clotting, it is unknown just how much longer blood would continue to flow from any wound where the Jones formulation was present. Also, the Jones formulation was not intended to promote healing or prevent infection in the event of a non-mortal hit of an animal, nor is there any indication that the ingredients in that formulation would have sufficient effectiveness in healing a wounded animal that escapes with such a wound.

OBJECTS AND SUMMARY OF THE INVENTION

It is an object of the present invention to provide blood trail enhancer that can be applied to hunting arrows and which will significantly slow the processes that cause blood trails to dry up.

It is another object to provide a blood trail enhancer treatment for the hunting arrows that delivers natural healing and anti-infection agents to the wound in the event of a less than mortal shot.

It is a further object to provide a blood trail enhancer treatment that can be applied to the head of the arrow, and to the distal end of the arrow shaft, and will not rinse off due to environmental moisture or rain.

In accordance with an aspect of the present invention, the blood trail enhancer is a composition of all-natural ingredients, including fish oil and apple cider vinegar, together with lesser amounts of ingredients that are both known anti-coagulants and known healing agents, such as garlic, onion, ginger, papaya, etc. The included ingredients are natural blood thinners, and/or natural anti-coagulants, and/or natural platelet inhibitors, and are also natural ingredients that promote healing and fight infections. It is desired to avoid synthetic ingredients, sedatives, muscle relaxants, or anaesthetic materials, as they may present health problems, if present in the meat that is later harvested from the animal.

The composition can be carried in a small plastic squeeze applicator, and can be applied from that directly onto the arrow broadheads and to the arrow shafts. The fish oil base prevents the treatment from being washed off due to rain. The applicator can be a small, one-ounce bottle, so the hunter can keep it handy during hunting.

According a to more particular aspect, the composition of the invention comprises fish oil and apple cider vinegar in respective amounts of 45 to 55 parts per hundred by volume and 25 to 35 parts per volume of the composition, and additional natural ingredient that inhibits blood clotting and promotes healing, in 5 to 10 parts by volume each of garlic, onion, and ginger. Papaya may also be used in some cases.

Some successful blood trail enhancers, which prolong the time before clotting up to fifteen to twenty minutes, can be formulated as follows (in amounts by volume):

a. fish oil—50; apple cider vinegar—30; garlic—10; onion—5; and ginger—5.

b. fish oil—47; apple cider vinegar—33; garlic—9; onion—6; and ginger—5.

c. fish oil—45; apple cider vinegar—35; garlic—10; onion—5; and ginger—5.

This composition can be applied to the arrows and arrowheads in advance of hunting and allowed to dry, or it can be applied to the arrows in the field. In either event, the composition, when used on the arrow broadhead and/or on the forward or distal end of the arrow shaft, will allow the hunter to find the killed or wounded deer or large game animal by the enhanced blood trail. Also, there will be a much better survival rate, i.e., better healing and infection fighting, for non-mortally wounded animals.

DETAILED DESCRIPTION OF THE PREFERRED EMBODIMENT(S)

The blood trail enhancer that I have formulated is composed of natural blood thinners and natural anti-pathogens including fish oil and apple cider vinegar, plus other ingredients including powdered ginger, powdered onion and powdered garlic, each of which has a strong anti-coagulent effect as well as an anti-pathogen effect. Other possible natural ingredients may be used, but not all combinations of ingredients mix well while other possible combinations may not achieve sufficient anti-coagulant effectiveness.

The protocol that was followed for testing the effectiveness of various formulations of the blood trail enhancer is that which is described in Hattersley, Paul G., *Activated Coagulation Time of Whole Blood*, Journal of the American Medical Association, May 2, 1966, page 150, ff., which is incorporated herein by reference. The Hattersley publication describes the protocol for measuring the active coagulation time (ACT) of whole blood, and involves drawing a small amount (1 ml) of blood (and other tissue juices) into a glass tube that contains diatomaceous earth, the tube being pre-warmed to body temperature (e.g., 37° C.), and starting a timer when blood appears in the tube. The tube is then tilted at five-second intervals, and is checked visually until the first unmistakable clot appears. For normal blood where no anti-clotting agents are present, this time will typically be between one and two minutes. For human patients who are administered blood thinners, the time may exceed two minutes, but usually will not exceed two minutes, thirty seconds.

This technique was used here to test coagulation of fresh blood in the presence of the agents that constitute the natural ingredients and that include compositions formulated as the preferred blood trail enhancers, as detailed below.

In compositions as tested in which there was significant delay in clotting, fish oil was present in an amount of between 55 and 70 parts per hundred, apple cider vinegar or ACV was present in an amount between 25 and 40 parts per hundred, and the balance was composed of the additional natural ingredients (i.e., ginger, garlic, onion, papaya, or the like).

First, the ACT was timed for blood (as a control) and then for blood in contact with each individual ingredient, with the results as follows:

| Test no. | Substance | Time (ACT) |
|---|---|---|
| 1 | Control | 1:48 (min:sec) |
| 2 | Papaya | 2:10 |
| 3 | Garlic liquid | 6:37 |
| 4 | Ginger liquid | 2:20 |
| 5 | Fish Oil | 3:30 |
| 6 | Onion powder | 2:50 |
| 7 | Garlic powder | 3:47 |
| 8 | Ginger powder | 3:00 |
| 9 | mix of all ingredients | 15+ minutes ** |

The protocol as described in the Hattersley article was followed in each test run. (** Note: when all ingredients were combined together and contacted with the blood sample in test 9, clotting was not detected after 15 minutes when the test was terminated.)

Subsequent to the above test runs, batches of the blood trail enhancer were prepared composed as follows, and each was contacted in turn with a blood sample, and the ACT was measured according to the Hattersley protocol. One drop of the composition was contacted with the blood in each test (except the Control).

Control: (blood alone); ACT=1:45;

Example I: Fish oil—70; garlic—10, ginger—10, onion—10 (parts per hundred); ACT=2:00;

Example II: Fish oil—80; garlic—10; ginger—5; onion—5; ACT=2:00.

Example III: ACV—80; Garlic—10; ginger—5; onion—5 (no fish oil); ACT=2:30;

Example IV: ACV—40; fish oil—40; garlic—10; ginger—5; onion—5; ACT=2:00;

Example V: ACV—45; fish oil—45; garlic—5; onion—5 (no ginger); ACT=3:08;

Example VI: ACV—30, fish oil(1)—50, garlic—10, onion—5, ginger—5; ACT=15:20;

Example VII: ACV—30; fish oil(2)—50; garlic—9; onion—6; ginger—5: ACT=20 minutes+.

(Notes: (1) in Example VI, a triple-strength pharmaceutical grade fish oil was used. (2) in Example VII, a pet grade fish oil was used, which had no flavorants or additives.)

Example VIII: ACV—33; fish oil (pet grade)—47; garlic—9; onion—6; ginger—5; ACT=20 minutes+;

Example IX: ACV—35; fish oil (pet grade)—45; garlic—10; onion—5; ginger—5; ACT=20 minutes+.

In the particularly effective compositions, namely, VI through IX, there was little odor to the composition after drying. These compositions seemed to mix well and seemed easy to dispense.

Because of the effect as described above on whole blood in a test situation, it is expected that there would be a similar prolonging of free blood flow from the wound when an animal suffers a mortal hit in archery hunting, and there would be adequate blood trail in most cases to lead the hunter to the game animal so it could be successfully harvested. The all natural ingredients also promote healing of the wound in the event the hit is not fatal, and also inhibit or combat infection from various pathogens, increasing the likelihood the animal will recover and survive after a non-lethal wound.

While the invention has been described in terms of preferred compositions and preferred modes of use, it should be appreciated that the invention is not limited to specific examples, but should be considered broadly, as defined in the appended claims.

I claim:

1. Natural blood trail enhancer composition, to be applied to head and shaft of a hunting arrow used in bow hunting to inhibit coagulation of blood at a wound site in a target game animal at a wound caused when the target game animal is struck by said arrow, and also to promote healing and prevent infection at the wound site when the wound is not fatal, the composition comprising:
   fish oil
   apple cider vinegar, and
   at least one additional natural ingredient that inhibits blood clotting and promotes healing, the at least one additional ingredient being selected from the group consisting of ginger, onion, garlic and papaya.

2. The composition of claim 1 wherein said fish oil and said apple cider vinegar are provided in respective amounts of 45 to 55 parts per hundred by volume and 25 to 35 parts per volume of the composition.

3. The composition of claim 2, wherein said at least one natural ingredient is provided in 5 to 10 parts by volume each of garlic, onion, and ginger.

4. The composition of claim 1, composed in amounts by volume as follows:
fish oil—50;
apple cider vinegar—30;
garlic—10;
onion—5; and
ginger—5.

5. The composition of claim 1 composed in amounts by volume as follows:
fish oil—47;
apple cider vinegar—33;
garlic—9;
onion—6; and
ginger—5.

6. The composition of claim 1 composed in amounts by volume as follows:
fish oil—45;
apple cider vinegar—35;
garlic—10;
onion—5; and
ginger—5.

7. A method of bow hunting of a target game animal employing one or more bowhunting arrows each having a shaft and a hunting arrow head mounted on a distal end of said shaft, the method comprising:
applying onto the head of the one or more arrows a composition to inhibit coagulation of blood of the target game animal and also to promote healing of a wound caused by the arrow when the wound is not fatal, the composition including
fish oil in an amount of 45 to 55 parts per hundred by volume;
apple cider vinegar in an amount of 25 to 35 parts per hundred by volume;
and the balance composed of additional natural ingredients with blood-coagulation inhibing properties and natural healing properties, namely, between five and fifteen parts per hundred by volume of garlic, onion, and ginger; and
launching one or more of said arrows at said target game animal.

8. The method of bow hunting of claim 7 wherein said composition is composed in amounts by volume as follows:
fish oil—50;
apple cider vinegar—30;
garlic—10;
onion—5; and
ginger—5.

9. The method of bow hunting of claim 7 wherein said composition is composed in amounts by volume as follows:
fish oil—47;
apple cider vinegar—33;
garlic—9;
onion—6; and
ginger—5.

10. The method of bow hunting of claim 7 wherein said composition is composed in amounts by volume as follows:
fish oil—45;
apple cider vinegar—35;
garlic—10;
onion—5; and
ginger—5.

11. The method of bow hunting of claim 7, including applying said composition onto the distal end of the shaft of said one or more arrows.

12. The method of bow hunting of claim 7, comprising, following the step of applying, allowing the composition to set and dry on said arrow head.

* * * * *